(12) United States Patent
Grispo et al.

(10) Patent No.: US 7,771,389 B2
(45) Date of Patent: Aug. 10, 2010

(54) INJECTOR AUTO PURGE

(75) Inventors: Keith M. Grispo, Plainfield, IL (US); Frank M. Fago, Mason, OH (US)

(73) Assignee: Mallinckrodt Inc., Hazelwood, MO (US)

( * ) Notice: Subject to any disclaimer, the term of this patent is extended or adjusted under 35 U.S.C. 154(b) by 816 days.

(21) Appl. No.: 11/073,892

(22) Filed: Mar. 7, 2005

(65) Prior Publication Data
US 2005/0182323 A1    Aug. 18, 2005

Related U.S. Application Data

(63) Continuation-in-part of application No. 10/780,269, filed on Feb. 17, 2004.

(51) Int. Cl.
*A61M 1/00* (2006.01)
*A61M 5/00* (2006.01)

(52) U.S. Cl. .................. 604/123; 600/432; 604/151

(58) Field of Classification Search ............ 604/67, 604/123–127, 151–155, 191, 284; 600/432
See application file for complete search history.

(56) References Cited

U.S. PATENT DOCUMENTS

| | | | |
|---|---|---|---|
| 4,044,757 A | 8/1977 | McWhorter et al. | |
| 5,236,417 A | 8/1993 | Wallis | |
| 5,472,403 A | 12/1995 | Cornacchia et al. | |
| 5,573,515 A * | 11/1996 | Wilson et al. | 604/236 |
| 5,662,612 A | 9/1997 | Niehoff | 604/155 |
| 5,814,015 A * | 9/1998 | Gargano et al. | 604/67 |
| 5,868,710 A | 2/1999 | Battiato et al. | 604/123 |
| 6,004,292 A | 12/1999 | Battiato et al. | 604/123 |
| 6,254,572 B1 * | 7/2001 | Knipfer et al. | 604/151 |
| 6,471,674 B1 | 10/2002 | Emig et al. | |
| 6,879,853 B2 | 4/2005 | Meaney et al. | |
| 6,917,828 B2 | 7/2005 | Fukuda | |
| 6,929,619 B2 * | 8/2005 | Fago et al. | 604/67 |
| 2004/0024361 A1 * | 2/2004 | Fago et al. | 604/152 |
| 2004/0073177 A1 * | 4/2004 | Hickle | 604/257 |
| 2004/0158205 A1 * | 8/2004 | Savage | 604/151 |

FOREIGN PATENT DOCUMENTS

JP    2-41173    2/1990

(Continued)

OTHER PUBLICATIONS

PCT/US2005/004600, *International Search Report and Written Opinion*, Jan. 9, 2005.

(Continued)

*Primary Examiner*—Kevin C Sirmons
*Assistant Examiner*—Andrew M Gilbert
(74) *Attorney, Agent, or Firm*—Marsh Fischmann & Breyfogle LLP

(57) ABSTRACT

An auto purge for an intravenous contrast injector of the type having a motor which advances a plunger drive ram and configured for use with a pre-filled or user-filled syringe containing an approximate known amount of air including a processor which causes the motor to move and a memory storing a predetermined purge stop point representative of the approximate known amount of air in the syringe, the injector configured to automatically advance the plunger drive ram an amount substantially equal to the predetermined purge stop point representative of the approximate known amount of air contained in the syringe.

27 Claims, 7 Drawing Sheets

FOREIGN PATENT DOCUMENTS

| | | |
|---|---|---|
| WO | WO 99/52575 | 10/1999 |
| WO | WO 01/37903 | 5/2001 |

OTHER PUBLICATIONS

Medrad, *Stallant CT Injection Systems—Dual Syringe,* Information Flyer and Instruction Manual pp. 3-32 and 3-33, no date.

Medrad, Inc., Stellant CT Injection System, Operation Manual Catalog #SOM 700 EN, 2003, 87 pages.

Medrad, Inc., Stellant CT Injection Systems, Platform Brochure, 2003, 4 pages.

Medrad, Inc., Medrad Launches New Standard in CT Injection Technology, Press Release, Apr. 2003, 3 pages.

* cited by examiner

INJECTOR AUTO PURGE

CROSS REFERENCE TO RELATED APPLICATION

This application is a continuation in part of previously filed U.S. application Ser. No. 10/780,269, filed Feb. 17, 2004, the entire content of which is hereby incorporated by reference.

FIELD OF THE INVENTION

The present invention relates generally to injectors for injecting fluids into patients and more particularly to purging air from such injectors.

BACKGROUND OF THE INVENTION

In many medical environments, a medical fluid is injected into a patient during diagnosis or treatment. One example is the injection of contrast media into a patient to improve nuclear medicine, Magnetic Resonance (MR), CT, optical, Angiographic, or Ultrasound imaging, using a powered, automatic injector.

Injectors suitable for these and similar applications typically must use a relatively large volume syringe and be capable of producing relatively large flow rates and injection pressures. For this reason, injectors for such applications are typically motorized, and include a large, high mass injector motor and drive train. For ease of use, the motor and drive train are typically housed in an injection head, which is supported by a floor, wall, or ceiling-mounted arm.

The injection head is typically mounted on the arm in a pivotal manner, so that the head may be tilted upward, with the syringe tip above the remainder of the syringe, to facilitate filling the syringe with fluid, and downward, with the syringe tip below the remainder of the syringe, for injection. Tilting the head in this manner facilitates removal of air from the syringe during filling, and reduces the likelihood that air will be injected into the patient during the injection process. Nevertheless, the potential for accidentally injecting air into a patient remains a serious safety concern, and if overlooked may be fatal in some instances.

In addition to the injection head discussed above, many injectors include a separate console for controlling the injector. The console typically includes programmable circuitry which can be used for automatic, programmed control of the injector, so that the operation of the injector can be made predictable and potentially synchronized with operations of other equipment such as scanners or imaging equipment.

Injector systems may also be configured with two heads. Respective syringes in each head are interconnected with tubing forming a "Y," or "Y-tubing," leading to a single intravenous injection site on a patient. For example, such syringes may contain a contrast media and a saline solution, and may be used in combination to prevent clotting.

One particular operational routine performed by the injector system is that of purging any air from the syringe, such as air introduced during filling, and any extension tubing used therewith. This purging sequence for a power injector typically requires that the operator tilt the head upright and advance the plunger so as to force any air from the syringe and extension tubing. This further reduces the likelihood that air will be injected into the subject during the injection process. This manual process is typically performed by trained clinicians to ensure reasonable efforts are taken to minimize or eliminate air from being injected into a patient.

Accordingly, a need exists to simplify the set-up sequence in power injectors so that an operator may automatically purge air from an injector prior to injection of a medical fluid into a patient.

In many applications, it is desirable to use an injector with multiple different size syringes. For example, it may be desirable to use a smaller syringe for pediatric use than for adult use. To facilitate the use of different syringe sizes, injectors have been adapted to include memory containing parameters for multiple different size syringes and to allow an operator to enter parameters or the type of syringe. Other injectors have been adapted to receive various heads specific to different syringes and select parameters for a syringe based thereon.

Irrespective of the particular size or construction of a syringe, each syringe may trap or contain a certain amount of air or gas based on the size or construction of the syringe. For example, one size of pre-filled syringe is produced with a small, e.g., approximately 1 milliliter (ml), nitrogen bubble to facilitate sterilization.

Accordingly, an auto purge for an injector need be adaptable to a variety of injectors. Further, an auto purge for an injector need work with pre-filled and/or empty syringes of varying sizes.

SUMMARY OF THE INVENTION

Those needs identified above and other problems of conventional injector systems are addressed by embodiments of the present invention which simplifies the set-up sequence in power injectors so that an operator may automatically purge air from an injector prior to injection of a medical fluid into a patient. Moreover, the present invention provides a method or auto purge routine that may be used with one or multiple injectors. In accordance with another aspect, the present invention may be used will pre-filled or user-filled syringes. In accordance with yet another aspect of the present invention, air may also be purged from any extension tubing that may be used the syringe.

A further aspect of the present invention relates to purging air from syringes used with an injector having two heads, each configured to receive one of the syringes. Such syringes are generally coupled to extension tubing, from which air may likewise be purged.

These and other features, aspects, objects, and advantages of the present invention will be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE INVENTION

Figure 1:
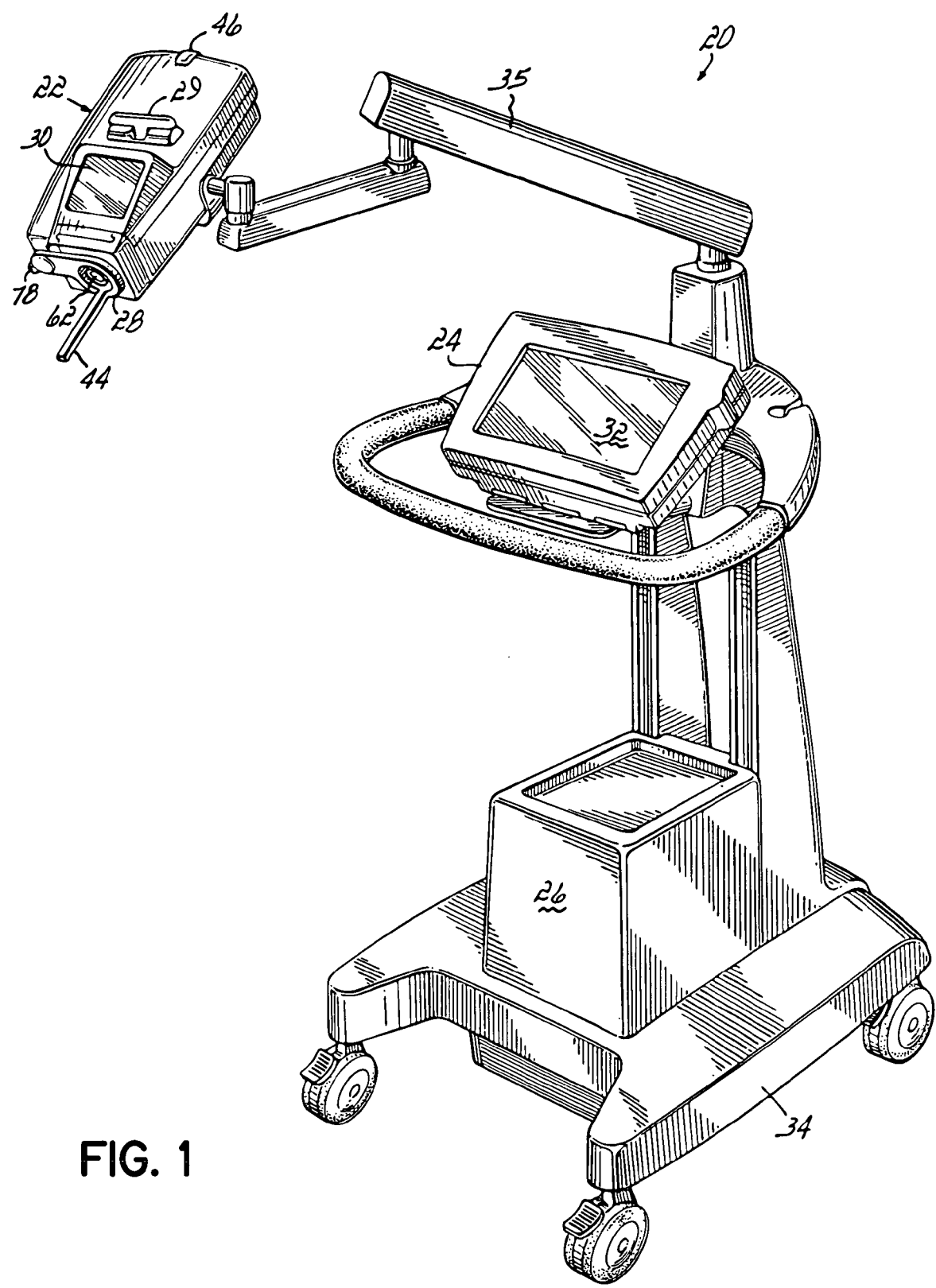
FIG. 1 illustrates a perspective view of an injector in accordance with principles of the present invention, including a power head, a console, and a power pack (under a cover), with the syringe, pressure jacket, heater blanket and air detection module removed.

Referring to FIG. 1, an injector 20 in accordance with the present invention includes various functional components, such as a power head 22, a console 24 and a power pack 26 (mounted inside of a cover). A syringe 36 (shown in FIG. 2) is mounted to the injector 20 in the face plate 28 of the power head 22, and the various injector controls are used to fill the syringe, e.g., user-filled syringe, with, e.g., contrast media for a nuclear medicine, Magnetic Resonance (MR), CT, optical, Angiographic, Ultrasound or other procedure, which media is then injected into a subject or patient under investigation under operator or pre-programmed control. It will be appreciated that a syringe may also be pre-filled.

The injector power head 22 includes a hand-operated movement control lever 29 for use in controlling the movement of the internal drive motor, and a display 30 for indicating to the operator the current status and operating parameters of the injector. The console 24 includes a touch screen display 32 which may be used by the operator to remotely control operation of the injector 20, and may also be used to specify and store programs for automatic injection by the injector 20, which can later be automatically executed by the injector upon initiation by the operator.

Power head 22 and console 24 connect through cabling (not shown) to the power pack 26. Power pack 26 includes a power supply for the injector 20, interface circuitry for communicating between the console 24 and power head 22, and further circuitry permitting connection of the injector 20 to remote units such as remote consoles, remote hand or foot control switches, or other original equipment manufacturer (OEM) remote control connections allowing, for example, the operation of injector 20 to be synchronized with the x-ray exposure of an imaging system.

Power head 22, console 24 and power pack 26 are mounted to a carriage 34 which includes a support arm 35 for supporting power head 22 for easy positioning of power head 22 in the vicinity of the examination subject. Other installations are also contemplated however; for example, console 24 and power pack 26 may be placed on a table or mounted on an electronics rack in an examination room while power head 22 is supported by a ceiling, floor or wall mounted support arm.

Figure 2:
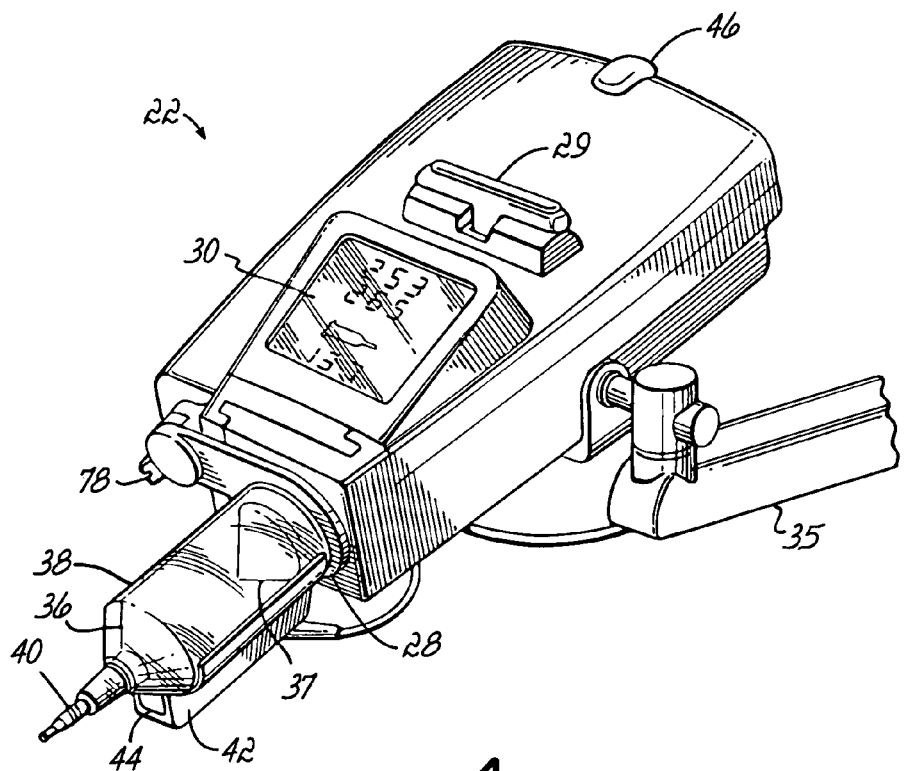
FIG. 2 illustrates a perspective view of the power head of the injector of FIG. 1 with a pressure jacket, syringe and heater blanket mounted thereto, showing the power head display, hand-operated control, and support arm mounting in greater detail.

Referring now to FIG. 2, in operation, a syringe 36 and pressure jacket 38 are mounted to power head 22, so that the motor internal to power head 22 may be energized to move plunger drive ram 62, shown in FIG. 1, and plunger 37 within the barrel of syringe 36 toward and away from a discharge tip 40 of the syringe, to thereby expel fluid from the syringe 36 or fill the syringe with fluid. Pressure jacket 38 provides support to the outer walls of syringe 36 to protect the walls of syringe 36 from failure at high injection pressures. It will be appreciated, however, that the use of a pressure jacket is not germane to the principles of the present invention, which may be applied to injectors regardless of whether they include a pressure jacket.

In the illustrated embodiment, syringe 36 and pressure jacket 38 are made of a clear plastic material through which the operator can view the current location of plunger 37 and any fluid or air in the syringe between plunger 37 and discharge tip 40. Accordingly, an operator may tilt power head 22 upward, fill syringe 36 from a source of fluid while visually monitoring the filling process, then connect the injector to tubing leading to (but not connected to) the patient, and expel, or purge, air from the tubing and syringe while visually monitoring the level of fluid in the syringe, and then once air has been expelled, tilt the injector downward, connect the tubing to the patient, and proceed to inject fluid into a subject.

To facilitate this filling and purging process, and other operations that may be performed during injection of a subject, power head 22 includes the hand-operated movement control, which is in the form of the rotatable lever 29. Specifically, lever 29 is rotatable on an axis of rotation inside of power head 22. When the hand-operated control lever 29 is left in its home position, illustrated in FIGS. 1 and 2, no plunger motion is generated by power head 22. However, when hand-operated control lever 29 is rotated toward syringe 36, forward plunger motion is generated by power head 22, expelling fluid or air from syringe 36. Alternatively, when hand-operated control lever 29 is rotated away from syringe 36, reverse plunger motion is generated by power head 22, filling syringe 36 with fluid or air.

Purging any air from the syringe, and any extension tubing used therewith, is typically performed by an operator. This also reduces the likelihood that air will be injected into the subject during the injection process. This manual purging procedure is also typically performed by, and generally requires, trained clinicians to ensure reasonable efforts are taken to minimize or eliminate air from being injected into a patient.

As will be described hereinafter, the present invention provides a routine for an injector that an operator may use to automatically purge air from a syringe and/or tubing prior to injection of a medical fluid into a patient. Moreover, and in accordance with principles of the present invention, an injector auto purge routine is adaptable to a variety of injectors and works with pre-filled and/or empty, e.g., user-filled, syringes of varying sizes.

To ensure that fluid injected into a subject is maintained at approximately body temperature, a heater blanket 42 is installed abutting the exterior wall of pressure jacket 38. Heater blanket 42 includes an electrical heater which generates heat for regulating the temperature of fluid within syringe 36. Heater blanket 42 is mounted to a post 44 extending from face plate 28, holding heater blanket 42 in thermal contact with pressure jacket 38.

At the rear end of power head 22 is an indicator lamp 46 (covered by a light-diffusing cover) which indicates the status of the power head.

Figure 3:
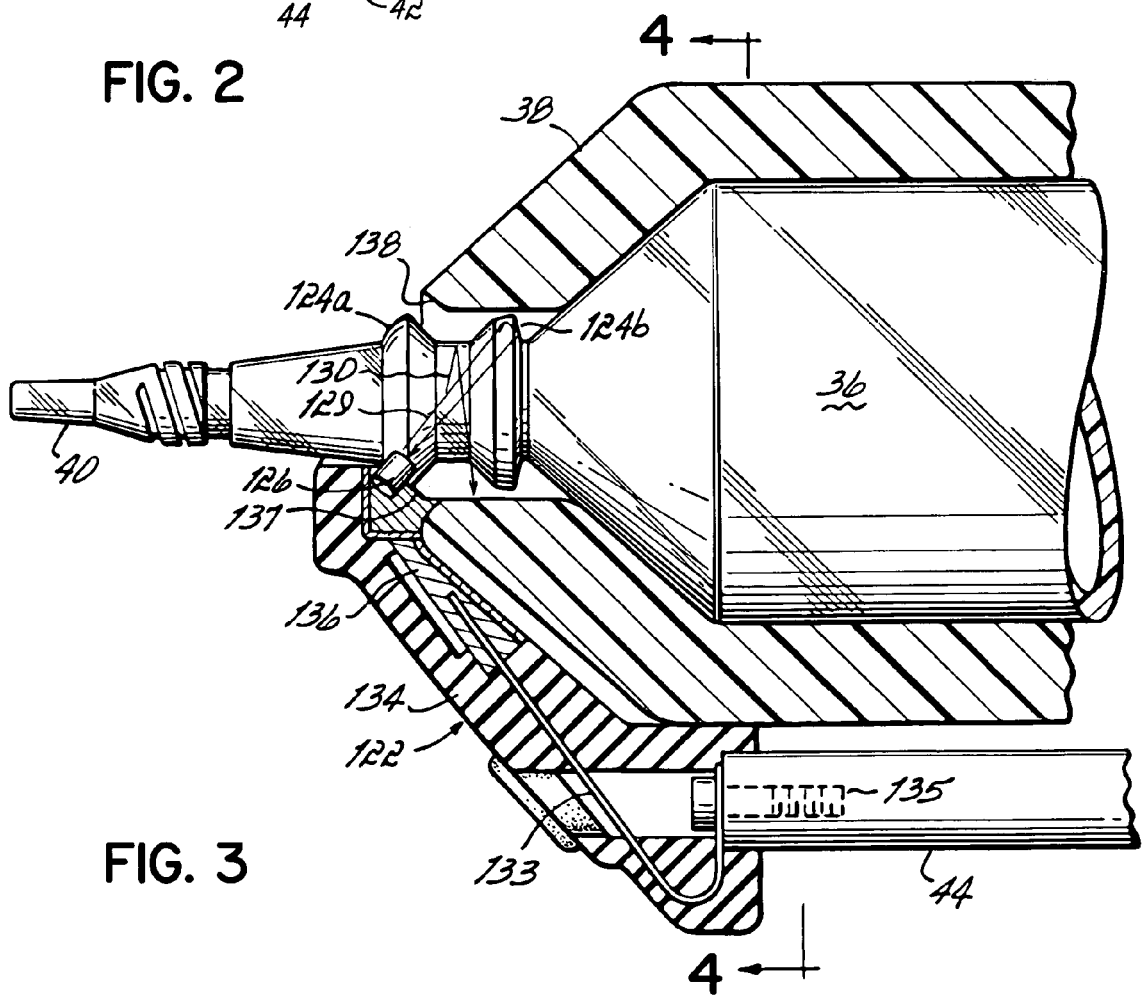
FIG. 3 is a partial cross-sectional view of a syringe mounted in the pressure jacket with the air detection module in place, showing the internal structure of the air detection module and its interaction with the structure of the syringe tip.
Figure 4:
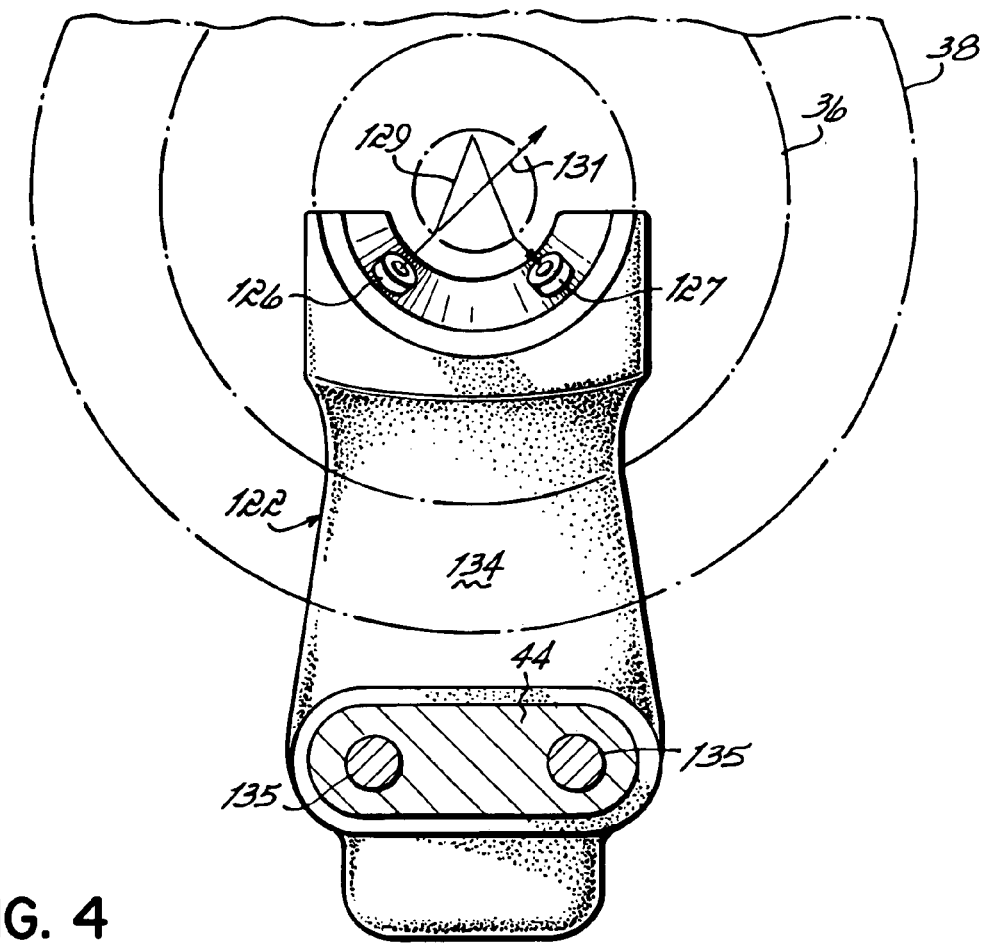
FIG. 4 is a view of the air detection module taken along lines 4-4 of FIG. 3, with the syringe and pressure jacket removed.

Referring now to FIGS. 3 and 4, the integral air detection system can be described. The air detection module 122 is mounted to the end of post 44, and is configured to wrap around the distal end of pressure jacket 38 and into contact with an outwardly projecting collar 124a surrounding the discharge neck of syringe 36. At the point of contact with collar 124*a*, the air detection module includes a light source 126 and light sensor 127. Light sensor 127 is a commercially available circuit, which includes sensor 127 and an oscillator which produces a trigger signal indicating when light source 126 should be stimulated to produce a light beam. The output of sensor 127 is a digital signal indicating whether the light beam is received by detector in response to triggering of the light source.

FIGS. 3 and 4 show illustrative ray traces showing the paths taken by light rays emitted from light source 126. Light source 126 includes an integral focusing lens, and collar 124*a* on the discharge neck of syringe 36 forms a second focusing lens. These lenses act in concert to direct light from light source 126 along path 129 toward collar 124*b* on the discharge neck of syringe 36. The internal shape of collar 124*b* forms a corner reflector, so that light impingent upon collar 124*b* from light source 126 is reflected toward light sensor 127.

As a result of this structure, when the neck of syringe 36 is filled with fluid, light rays emitted from light source 126 follow paths through the neck of syringe 36, which reflect and return to light sensor 127, such as path 129 illustrated in FIGS. 3 and 4. Accordingly, under such conditions, sensor 127 will produce a digital signal indicating receipt of light, which indicates the absence of air in the syringe neck. (The combined focal length of the lens in light source 126 and collar 124*a*, is longer than the distance traveled by light along path 129, i.e., longer than twice the distance between collar 124*a* and collar 124*b*.)

However, when the neck of the syringe contains air or an air bubble, diffraction of light at air/fluid or air/syringe boundaries will cause light to deviate substantially from the path 129 illustrated in FIGS. 3 and 4. Specifically, light rays incident in the neck of syringe 36 might follow the path 130 illustrated in FIG. 3, or the path 131 illustrated in FIG. 4. In either circumstance, the presence of the air bubble prevents light from reflecting through the neck of the syringe from light source 126 to light detector 127, thus causing the light detector to produce a signal indicating failure to receive light, indicating that air is present in the neck of the syringe.

To ensure consistent, repeatable results, air detection module 122 is structured to ensure solid contact between light source 126, light sensor 127 and the surface of collar 124*a* on syringe 36. Specifically, the air detection module 122 has a spring-metal interior skeleton 133, which is over molded with a soft flexible plastic 134. One end of spring metal skeleton 133 is mounted to post 44 by mounting screws 135 (which are accessible via voids in the plastic overmold 134). The opposite end of skeleton 133 supports the air detector module, which includes a hard plastic molding 136 supporting the light source 126 and light sensor 127. Molding 136 includes a beveled section 137 sized to fit into a chamfer 138 at the aperture of pressure jacket 38. The interaction of beveled section 137 and chamfer 138 ensure precise positioning of light source 126 and light sensor 127 relative to pressure jacket 38.

The neck of the syringe 36 is sized with a slight interference fit, so that collar 124*a* contacts and slightly deflects air detection module 122 when the syringe 36 is inserted into pressure jacket 38, flexing spring skeleton 133 and resulting in a steady application force of light source 126 and light sensor 127 against collar 124*a* of syringe 36. This application force ensures good communication of light from source 126 into the neck of syringe 36 and from the neck of syringe 36 into light sensor 127.

Further details of exemplary hardware and software which control operation of an injector system such as that illustrated in FIGS. 1-4 can be found in U.S. Pat. No. 5,868,710 which is assigned to the assignee of the present invention and incorporated herein by reference, in its entirety.

An injector system, such as injector 20, may include alternative methods of ascertaining syringe parameters, those syringe parameters relating either to, or including, the amount of air or gas that may be trapped or contained in a syringe and any extension tubing used therewith. For example, syringe parameters may be entered into injector 20 by a service technician. Syringe parameters may also be derived from face plate 28 particular to syringe 36, and that adapts injector 20 for use with that syringe 36. Face plate 28 may be locked or engaged in position on power head 22 using position cam lever 78 to facilitate the acquisition of such syringe parameters. Each of these alternative methods will, in turn, be described in some detail, as follows.

Referring once again to FIG. 1, and as mentioned, console 24 and touch screen display 32 offer a user interface for an operator of the injector 20. Because the functionality related to maintaining injector 20 generally differs from that utilized by an operator, service personnel are typically provided an interface screen on the console different from an operator's interface screen. From this service interface screen, a technician may be offered a menu selection to add, or to modify, the stored definition of a syringe's physical characteristics.

The service technician may then provide input to the user interface via the input devices (e.g., keyboard, touchscreen, etc.) that are part of the injector 20 or from other diagnostic equipment which can connect to interface ports of the injector 20. The service technician may thereby use the console 24 to reach the service user interface provided by injector 20 and select, from among a plurality of service-related choices, a routine that permits changing of the stored syringe definitions. Moreover, this particular service routine permits the technician to specify whether the intended change is creating a new syringe definition or changing an existing definition. If changing an existing definition, the technician can be presented with the names of stored syringes to aid with selecting the right definition to update.

In accordance with an aspect of the present invention, a technician may also enter information describing the amount of gas and/or air in a syringe and any extension tube used therewith. In accordance with another aspect of the invention, a technician may also enter a value associated with an equivalent volume related to the mechanical clearance between a plunger driver ram 62 and a syringe plunger 37. Also, the interface will preferably provide an opportunity for the service technician to label, or otherwise designate, the new syringe information. Doing so will allow an operator to more easily select the correct syringe when operating the injector.

Further details of the wide variety of protocols and routines which an injector system can automatically perform using stored syringe definitions and related parameters can be found in U.S. Pat. No. 5,662,612 which is assigned to the assignee of the present invention and incorporated herein by reference, in its entirety. Moreover, syringe parameters associated with the amount of gas and/or air in a syringe and any extension tube used therewith, as well as any equivalent volume related to the mechanical clearance between a plunger drive ram and a syringe plunger may also be entered.

As mentioned, syringe parameters may also be derived from face plate 28 particular to syringe 36, and that adapts injector 20 for use with that syringe 36. Again, face plate 28 may be locked or engaged in position on power head 22 using position cam lever 78 to facilitate the acquisition of such syringe parameters.

Figure 5:
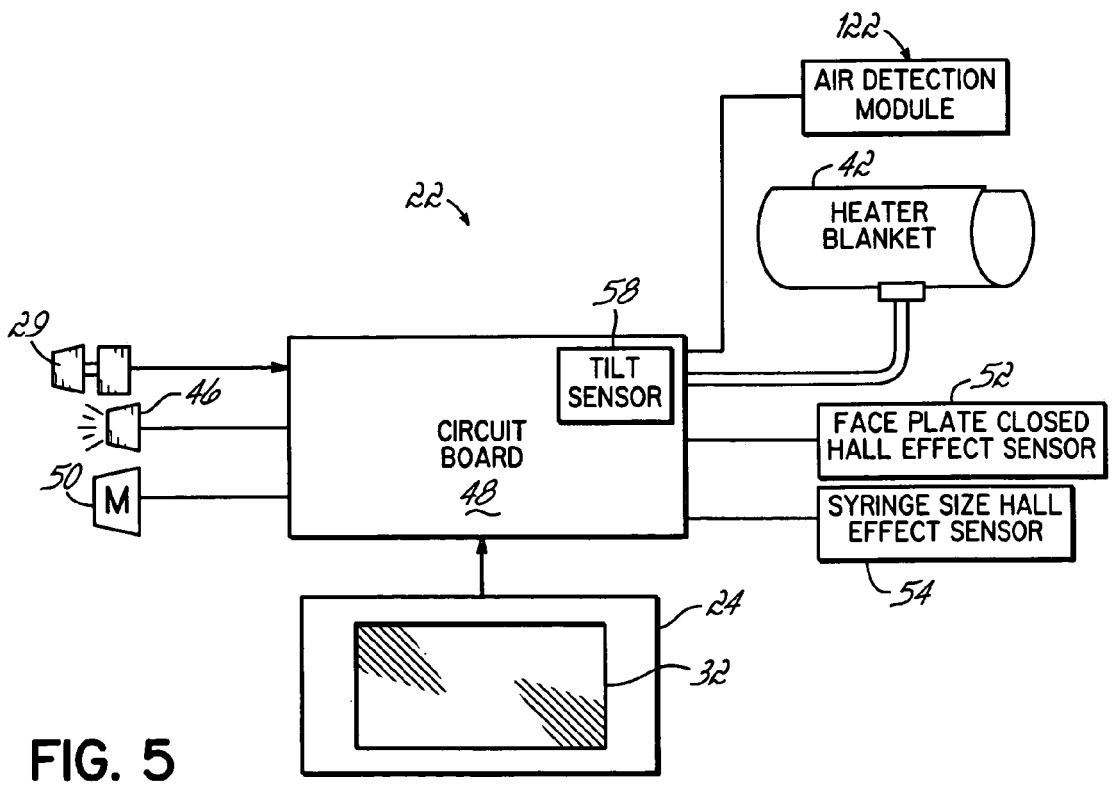
FIG. 5 illustrates an electrical and electromechanical block diagram of the power head shown in FIGS. 1-4.

Referring now to FIG. 5, an electrical and electromechanical block diagram of the power head 22 shown in FIGS. 1-4 is shown. Power head 22 comprises a circuit board 48 including a microprocessor to perform communications with power pack 26. Circuit board 48 receives and/or forwards input or "touches" from touch screen 32 on console 24, and, thus, circuit board 48 including its microprocessor may receive syringe parameters as described above.

Circuit board 48 also detects the output of two Hall effect sensors 52, 54. As described, power head 22 has a removable face plate 28, shown in FIGS. 1 and 2. There may be multiple face plates having differently-sized apertures for accepting differently-sized syringes. Thus, although face plate 28 need not be removed to replace syringe 36 with another like sized syringe, face plate 28 may be removed to used a different sized syringe.

Circuit board 48 also receives electrical pulses indicating movements from lever 29 mounted atop power head 22 and lights and extinguishes light 46 mounted at the rear of power head 22. Circuit board 48 also controls a motor 50 coupled to a gear box that translates the rotary motion of the motor to linear translation of plunger drive ram 62 and plunger 37 of syringe 36. Circuit board 48 controls heater blanket 42 which heats a contrast fluid in the syringe. Further, circuit board 48 detects the output of air detection module 122.

Circuit board 48 may further include a single-chip accelerometer configured as a tilt sensor 58. Sensor 58, mounted to circuit board 48, is configured to produce an analog voltage indicative of the tilt of power head 22 relative to the direction of Earth gravity. Moreover, sensor 58 may be used to detect any angle power head 22 is positioned in. Thus, sensor 58 may used to detect whether discharge tip of syringe 36 is pointed up or down, and since air will generally accumulate at the discharge tip when the tip is pointed up, an auto purge routine may be configured to operate only when a discharge tip is pointed generally in an upward position.

Those skilled in the art will appreciate that a mercury switch may be alternatively used to detect whether discharge tip of syringe 36 is pointed up or down. Similarly, a mechanical switch and a switch actuator may also be used. Irrespective of the type of sensor used, an auto purge routine may be configured to operate only when a discharge tip is pointed generally in an upward position.

Sensor 52 detects whether face plate 28 has been locked into position using position cam lever 78 on power head 22, and if not circuit board 48 discontinues energizing motor 50, thereby preventing any further injection procedures until such time as a face plate is locked into position. Sensor 54 detects the size of the face plate in use. Moreover, this information is forwarded to circuit board 48 including the microprocessor whereby this information is associated with syringe parameters, e.g., size and type, and is used to controlling motor 50 and any syringe coupled thereto.

Irrespective of whether syringe parameters are entered from a user interface, stored in memory, and recalled for later use in controlling a syringe plunger, or derived from a face plate adapted for use with a particular size syringe, or some combination thereof, an injector auto purge routine in accordance with principles of the present invention may be developed. Moreover, air detection may also be used in such a routine.

Figure 6:
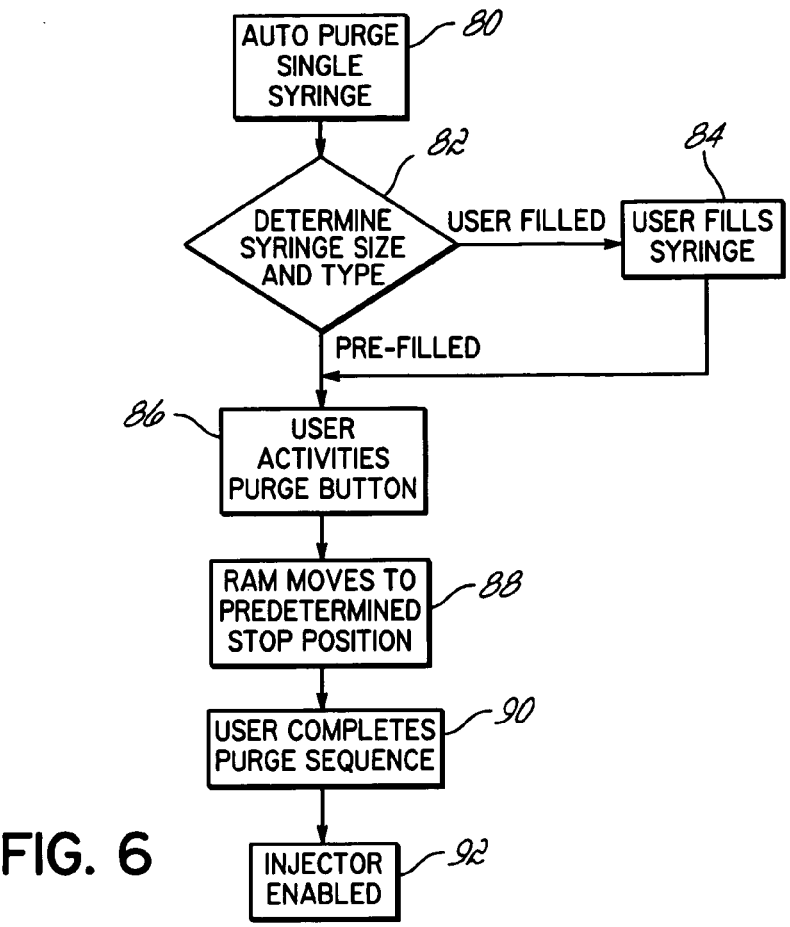
FIG. 6 is a flow chart for an injector auto purge routine for an injector having a single syringe.

Before describing the programmatic flow of routine 80, shown in FIG. 6, a brief description of an exemplary syringe with an associated extension tube coupled thereto will be provided. It is this exemplary syringe and extension tubing that will be used as a backdrop for the description of routine 80, and routines 94 and 140 in FIGS. 7 and 10, respectively.

Figures 8, 9:
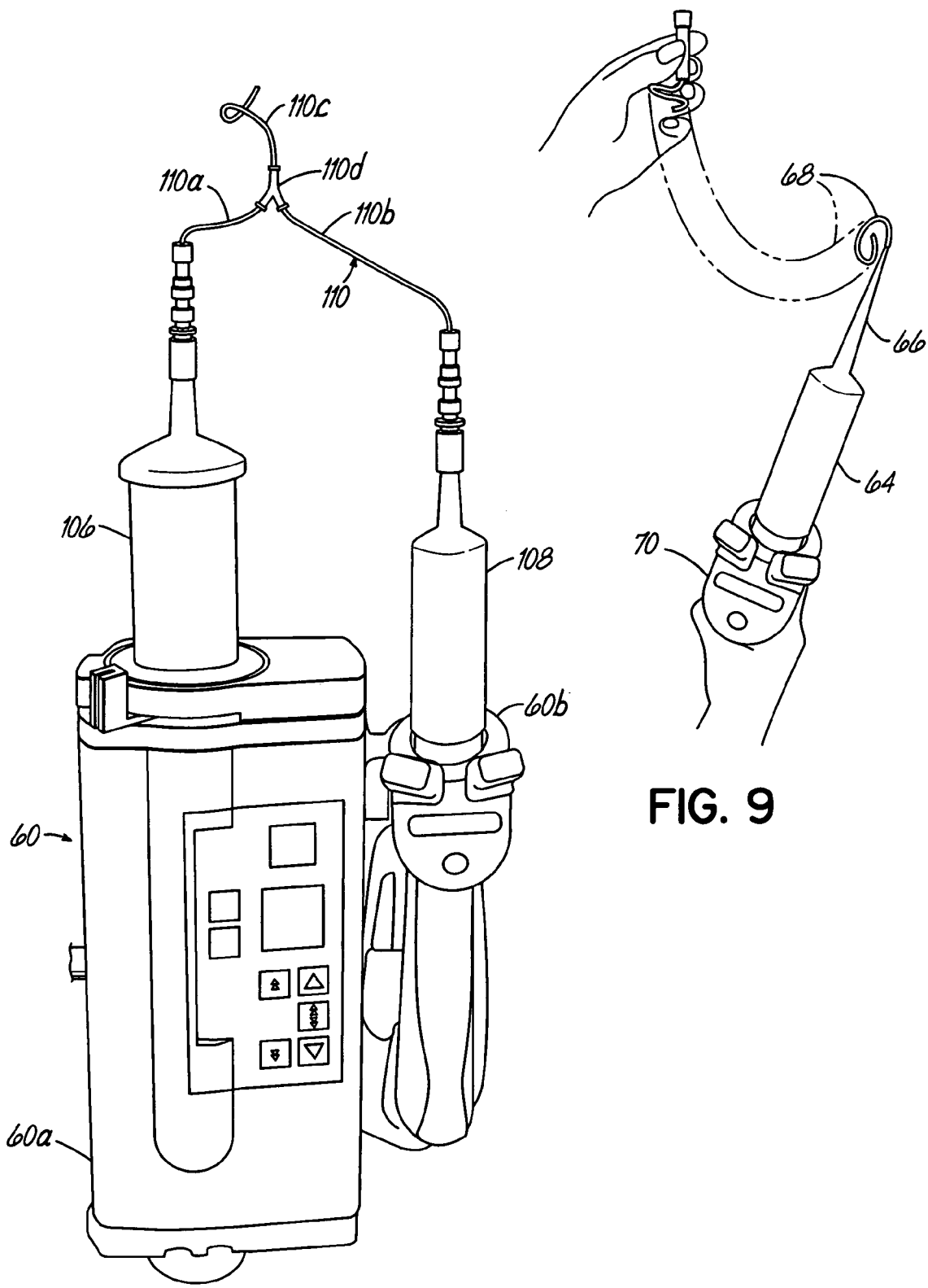
FIG. 8 illustrates a perspective view of a dual head injector in accordance with principles of the present invention.
FIG. 9 illustrates a perspective view of the hand-held portion of the dual head injector of FIG. 8.

Referring now to FIG. 9, exemplary syringe 64 is one of many particularly sized pre-filled syringes produced with a small, e.g., approximately 1 milliliter (ml), nitrogen bubble to facilitate sterilization. Such a small nitrogen bubble is generally contained within discharge tip 66 when syringe 64 is oriented in an upright position as shown in FIG. 9. Associated with and coupled to syringe 64 is extension tubing 68. Extension tubing 68 is a pragmatic consideration in reaching an injection site on a patient. Extension tube 68 is of a diameter commonly used with syringe 64 and is sixty inches (60") long. As such, extension tubing 68 contains 2.5 ml of air. A further consideration is the clearance between an injector plunger drive ram (e.g., plunger drive ram 62 shown in FIG. 1) and a syringe plunger (e.g., syringe 36 plunger 37 shown in FIG. 2). For syringe 64 and injector 70 (which is a hand-held head 60b, better shown in FIG. 8, and will be discussed in more detail hereinafter), this is the equivalent of approximate 3 ml. Thus, the total amount of gas and/or air that desired to be purged is 6.5 ml.

Those skilled in the art will appreciate that other assumptions may be made regarding the amount of air trapped during filling of an empty syringe, due to aeration during filling the syringe. These may be based on, for example, the volume of the syringe and the contrast media used. Further, those skilled in the art will appreciate that assumptions may be based on historical data and/or experience.

With exemplary pre-filled syringe 64 and extension tubing 68 in mind, and referring once again to FIG. 6, a flow chart for an injector auto purge routine 80 for an injector having a single syringe, such as injector 20 shown in FIGS. 1-5, is illustrated. As will be appreciated by one of ordinary skill in the art having the benefit of the instant disclosure, an injector generally operates under the control of a processor, and executes or otherwise relies upon various computer software, components, programs, objects, modules, data structures, etc. Moreover, various applications, components, programs, objects, modules, data structures, etc. may also execute on one or more processors in an injector, i.e., the processing required to implement various functions of a routine may be allocated to multiple processors within the injector.

In general, the routines executed to implement the embodiments of the present invention, whether implemented as part of an operating system or a specific application, component, program, module, or sequence of instructions, or even a subset thereof, will be referred to herein as a program or "routine." A routine typically comprises one or more instructions that are resident at various times in memory and storage devices in an injector, and that, when read and executed by one or more processors in an injector, causes the injector to perform the various steps necessary to execute steps or elements embodying the various aspect of the invention. Moreover, while the invention has and hereinafter will be described in the context of fully functioning injectors, those skilled in the art will appreciate that the various embodiments of the invention are capable of being distributed as a program product in a variety of forms, and that the invention applies equally regardless of the particular type of signal bearing media used to actually carry out the distribution. Examples of signal bearing media include, but are not limited to, recordable type media such as volatile and non-volatile memory devices, floppy and removable disks, hard disk drives, magnetic tape, optical disks (e.g., CD-ROMs, DVDs, etc.), among others, and transmission type media such as digital and analog communications.

In addition, various routines described hereinafter may be identified based upon the application within which it is implemented in a specific embodiment of the invention. However, it should be appreciated that any particular program or routine nomenclature that follows is used merely for convenience, and thus the invention should not be limited to use solely in any specific routine identified and/or implied by such nomenclature. Furthermore, given the typically endless number of manners in which program functionality may be organized into routines, procedures, methods, modules, objects, and the like, as well as the various manners in which program functionality may be allocated among various software layers that are resident within a typical injector, it should be appreciated that the invention is not limited to a specific organization and allocation of routine functionality described herein.

Those skilled in the art will recognize that the exemplary routine illustrated in FIG. 6 is not intended to limit the present invention. Indeed, those skilled in the art will recognize that other alternative hardware and/or software environments may be used without departing from the spirit of the present invention.

Auto purge routine 80 begins execution in step 82. In step 82, the syringe size and type is determined, for example, using hall effect sensor 54. Pre-filled syringes are commonly available in sizes including 50, 75, 100 and 125 milliliters (mL), whereas empty or user-filled syringes may be available in sizes up to, and including, 200 mL. If it is determined that the syringe must be user-filled, execution proceeds to step 84, wherein the user is prompted to fill the syringe, and whereafter execution proceeds to step 86. However, if instead, it is determined that the syringe is pre-filled, execution proceeds immediately to step 86, and the user is prompted to press or activate a purge button.

As shown in step 88, once the purge button is pressed, a plunger drive ram, such as plunger drive ram 62, moves to a predetermined stop point based on the syringe parameters determined or gathered in step 82, forcing air and/or gas from the syringe, e.g., syringe 36. In step 90, the user completes the purge sequence, such as by articulating lever 29 to force any remaining air and/or gas from syringe 36. Finally, in step 92, the injector is enabled, and the user may proceed with injecting a medical fluid into a patient.

Thus, auto purge routine 80 simplifies the set-up sequence in power injectors so that an operator may automatically purge air and/or gas from an injector prior to injection of a medical fluid into a patient. Moreover, auto purge routine 80 for an injector is adaptable to a variety of injectors, and works with pre-filled and/or empty syringes of varying sizes.

In an alternative embodiment of the invention, the completion of the purge sequence in step 90 may involve additional program steps as will be elaborated below with reference to FIG. 11.

Figure 7:
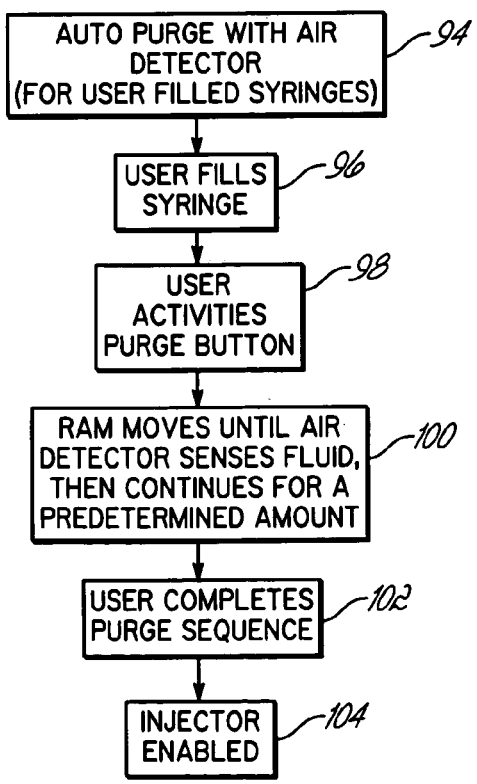
FIG. 7 is a flow chart for an injector auto purge routine for an injector including an air detector.

Referring now to FIG. 7, a flow chart for an injector auto purge routine 94 for an injector including an air detector is illustrated. More specifically, routine 94 is for use with user-filled syringes, though those of skill in the art may readily adapt routine 94 for use with pre-filled syringes.

Routine 94 begins execution in step 96, wherein a user fills a syringe with a medical fluid. Next, in step 98, the user is prompted to press or activate a purge button. As shown in step 100, and once the purge button is pressed, a plunger drive ram, such as plunger drive ram 62, advances or moves until an air detector, such as air detection module 122, senses fluid, and then continues for a predetermined amount, forcing any and/or gas from the syringe. Such a predetermined amount, and an associated stop position, may be based on an assumed extension tubing size. Exemplary extension tubing will shown in FIGS. 8 and 9, and discussed in more detail hereinafter.

Next, in step 102, the user completes the purge sequence, again, such as by articulating lever 29 to force any remaining air and/or gas from syringe 36. Finally, in step 104, the injector is enabled, and the user may proceed with injecting the medical fluid into a patient.

In an alternative embodiment of the invention, the completion of the purge sequence in step 102 may involve additional program steps as will be elaborated below with reference to FIG. 11.

Thus, auto purge routine 94 simplifies the set-up sequence in power injectors so that an operator may automatically purge air and/or gas from an injector prior to injection of a medical fluid into a patient. Moreover, auto purge routine 80 for an injector is adaptable to a variety of injectors, and works with empty or user-filled syringes of varying sizes.

Those skilled in the art will also recognize that the exemplary routine illustrated in FIG. 7 is also not intended to limit the present invention. Indeed, those skilled in the art will recognize that other alternative hardware and/or software environments may be used without departing from the spirit of the present invention.

Referring now to FIG. 8, a perspective view of a dual head injector 60 is illustrated. Dual head injector 60 comprises a mounted head 60a and a retractable or hand-held head 60b. Mounted head 60a and hand-held head 60b are configured to receive syringes 106, 108, respectively. The ram of hand-held head 60b is actuated by a purge/retract trigger that moves the ram proportionally to the amount that the trigger is depressed. Dual head injector 60 may be configured to purge air and/or gas from respective syringes 106, 108 and "Y-tubing" 110, mounted head 60a and hand-held head 60b being in electronic communication with one another.

Y-tubing 110 comprises three sections of tubing 110a-c and connector 110d. Tubing sections 110a and 110b are coupled to syringes 106 and 108, respectively, and connector 110d. Tubing section 110c is also coupled to connector 110d and typically provides connectivity with a patient injection site (not shown).

Dual head injector 60 is configured to purge the air from Y-tubing 110 in a manner similar to that described above. For example, head 60a may contain a contrast media, while hand-held head 60b may contain a saline solution for use therewith. In such case, head 60a first purges air from tubing 110a up to the intersection of Y-tubing 110 at connector 110d. Hand-held head 60b then purges the remaining air from tubing 110b, connector 110d, and tubing 110c, thereby substantially purging all air and/or gas from injector 60. The sequencing of purging is controlled though electronic communication of mounted head 60a and hand-held head 60b as will be appreciated by those of skill in the art.

Those skilled in the art will appreciate that filling the tubing with saline has several advantages. First, the saline may be used to keep venous access to a subject patient clear of blood clots. Second, the saline may be used as a test injection to check for extravasation. Third, the saline may help to compact the medical fluid, such as a contrast media, keeping the contrast media together.

Figure 10:
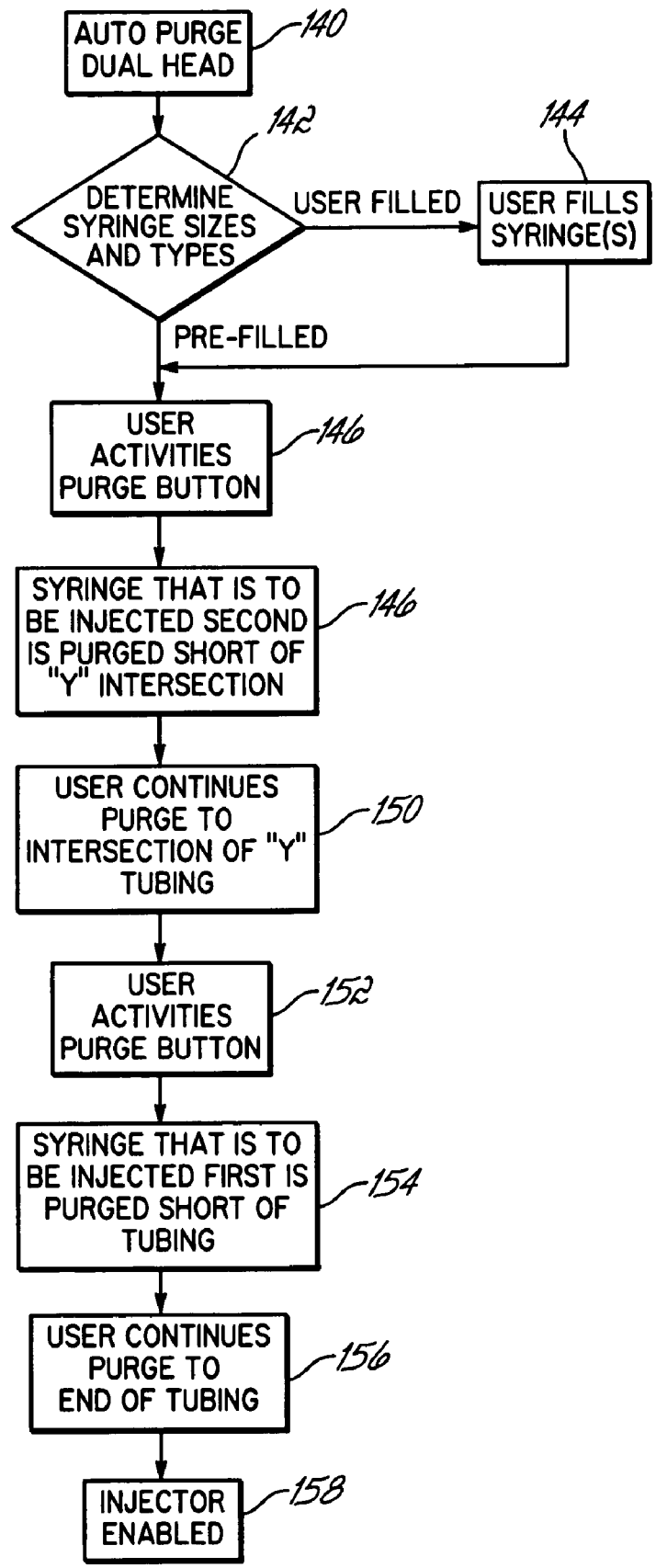
FIG. 10 is a flow chart for injector auto purge routine for a dual head injector.

Referring now to FIG. 10, a flow chart for injector auto purge routine 140 for a dual head injector is illustrated. For example, auto purge routine 140 may be used with dual head injector 60 shown in FIG. 8, head 60a containing a contrast media and being referred to as the syringe that will be injected second, or the second syringe, and hand-held head 60b containing a saline solution and being referred to as the syringe that will be injected first, or the first syringe.

Auto purge routine 140 begins execution in step 142 wherein the syringe sizes and types, e.g., syringes 106, 108, are determined. Again, pre-filled syringes are commonly available in sizes including 50, 75, 100 and 125 mL, whereas empty or user-filled syringes may be available in sizes up to, and including, 200 mL. If it is determined that one or both of the syringes must be user-filled, execution proceeds to step 144, wherein a user is prompted to fill the syringes, and where after execution proceeds to step 146. However, if instead, it is determined that the syringes are pre-filled, execution proceeds immediately to step 146, and the user is prompted to press or activate a purge button.

In step 148, once the purge button is pressed, a plunger drive ram for the syringe that is to injected second, e.g., head 60a and syringe 106, moves to a predetermined stop point based on the syringe parameters determined or gathered in step 142, forcing air and/or gas from the syringe and the tubing connected thereto, or tubing 110a. In step 150, the user manually completes the purge sequence for the second syringe, using a manual knob or expel buttons, forcing any remaining air and/or gas from syringe 106 and tubing 110a, up to the intersection of Y-tubing 110 in connector 110d.

Next, in step 152, the user is again prompted to press or activate the purge button. In step 154, and once the purge button is pressed, a plunger drive ram for the syringe that is to injected first, e.g., head 60b and syringe 108, moves to a predetermined stop point based on the syringe parameters determined or gathered in step 142, forcing air and/or gas from the syringe and the tubing connected thereto, or tubing 110b, connector 110d, and tubing 110c. In step 156, the user manually completes the purge sequence for the first syringe, using a manual knob or expel buttons, forcing any remaining air and/or gas from syringe 108 and tubing 110b, connector 110d, and tubing 110c.

Finally, in step 158, the injector is enabled, and the user may proceed with injecting the medical fluid, or contrast media, and/or the saline solution into a patient.

In an alternative embodiment of the invention, the completion of the purge sequence in step 156 may involve additional program steps as will be elaborated below with reference to FIG. 11.

Thus, auto purge routine 140 simplifies the set-up sequence in power injectors so that an operator may automatically purge air and/or gas from an injector prior to injection of a medical fluid into a patient. Moreover, auto purge routine 140 is for a dual head injector, and is adaptable to a variety of injectors, working with pre-filled and/or empty syringes of varying sizes.

Figure 11:
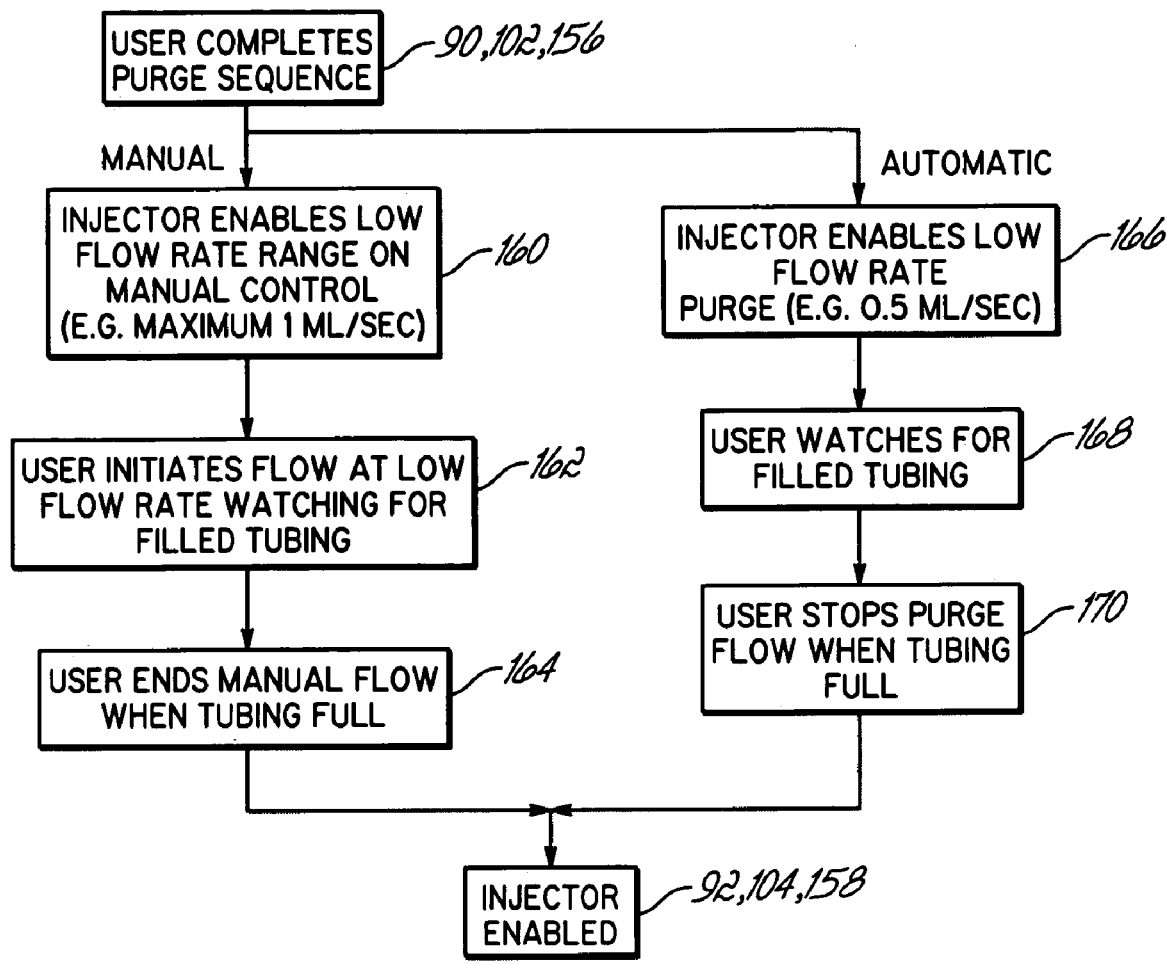
FIG. 11 is a flow chart of a routine for completing a purge using a low flow rate.

Referring now to FIG. 11, an alternative embodiment of the invention for completing a purge sequence is illustrated. As noted above, in steps 90, 102 and 156 of FIGS. 6, 7 and 10, respectively, the user completes the purge sequence after the injector automatically purges to a predetermined stop point, which is typically short of a completely expelled position. The user may expel the remaining air from the syringe under manual control, or may initiate automatic expelling movement of the ram, and then manually stop that movement when air has been completely purged. A difficulty with either approach is that the speed of motion that is automatically or manually created may be excessive. For example, a typical purge flow rate of 8 ml/sec will create rapid fluid movement in the tubing and syringe extension—a rate of only 0.5 ml/sec will translate to fluid movement of 10 inches/second in tubing. The user wishes to end purging flow after the fluid boundary is less than an inch past the end of the tubing, which implies that the user must have a reaction time of less than a second at typical purging flow rates. Even when using a manual movement control such as described above, it is difficult to control flow rates to the low level required for accurate purging of the fluid boundary to within an inch of a desired location.

Accordingly, in an embodiment of the present invention, the user is provided a feature for accurate low flow rate purging as the last step of a purging routine. Specifically, in an embodiment using an adjustable manual movement control such as control 29 shown in FIG. 1, when the injector reaches step 90, 102 or 156, the injector then enables a low flow rate range for the manual movement control, e.g., with a maximum flow rate of 1 ml/sec. Then in step 162, the user uses the manual control to purge the remaining air from the tubing using the manual control operating in this low flow rate range, which watching for the moment when the fluid just fills the connecting tubing. Finally, in step 164, the user ends the manual flow by returning the manual control to a "stop" position when the tubing is full. Thereafter, the injector is enabled in step 92, 104 or 158 and the injector disables the low flow rate range for the manual movement control.

In an alternate embodiment of the present invention, when the purge sequence is completed in step 90, 102 or 156, in step 166 the injector enables (and/or the user is prompted to initiate or initiates manually) a low flow rate purging operation, in which fluid is purged at a steady slow flow rate of, e.g., 0.5 ml/sec. While the injector continues this manual purging in step 168 the user watches for the moment when the fluid just fills the connecting tubing. Finally, in step 170, the user stops the purge flow, e.g., by depressing a button or actuating another control on the injector, when the tubing is full. Thereafter, the injector is enabled in step 92, 104 or 158 and the injector continues normal operation.

The inclusion of a low flow rate completion step as described may substantially enhance the usability of an injector and improve the purging of fluid and reduce associated waste and spillage of fluid.

While the present invention has been illustrated by description of various embodiments and while these embodiments have been described in considerable detail, it is not the intention of the applicant to restrict or in any way limit the scope of the claims to such detail. Additional advantages and modifications will readily appear to those skilled in the art. For example, in an injector having a tilt sensor, the routines of FIGS. 6, 7 and 10 may be enhanced by including therein steps for determining whether the injector is tilted upright as a precondition to performing a purge operation, to ensure captured air is adjacent the syringe neck and discharge outlet while purging. The invention in its broader aspect is, therefore, not limited to the specific details, representative system, apparatus, and method, and illustrative example shown and described. Accordingly, departures may be made from such details without departing from the spirit or scope of the applicant's general inventive concept.

What is claimed is:

1. A medical fluid injector comprising:
   a syringe having:
      a barrel that includes a discharge tip; and
      a plunger disposed within and movable relative to the barrel;
   a motorized plunger drive ram configured to move the plunger of the syringe within and relative to the barrel of the syringe both toward and away from the discharge tip of the syringe;
   a processor which controls movement of the plunger drive ram, the processor configured with a purge sequence designed to force air and/or gas from the syringe via the discharge tip prior to fluidly connecting the syringe with a patient, the processor being further configured with an injection protocol designed to inject medical fluid into a patient when the syringe is fluidly connected with a patient; and a tilt sensor, wherein an output from the tilt sensor allows for execution of the purge sequence only when the discharge tip of the syringe is pointed upward, wherein an output from the tilt sensor allows for execution of the injection protocol when the discharge tip of the syringe is pointed downward, and wherein the purge sequence includes:
- the plunger drive ram moving the plunger within the barrel of the syringe and toward the discharge tip of the syringe an amount substantially equal to a predetermined stop point; and
- a low flow rate that is enabled upon the plunger drive ram reaching the predetermined stop point, wherein the low flow rate is a flow rate at which medical fluid is expelled from the discharge tip of the syringe due to the plunger drive ram moving the plunger within the barrel of the syringe, and wherein the low flow rate is no more than about 1 ml/sec.

2. The injector of claim 1, wherein the low flow rate is no more than about 0.5 ml/sec.

3. The injector of claim 1, wherein the medical fluid comprises contrast media.

4. The injector of claim 1, wherein the syringe is designed to allow medical fluid to enter the barrel thereof via the discharge tip.

5. The injector of claim 4, wherein the low flow rate is no more than about 0.5 ml/sec.

6. The injector of claim 4, wherein the syringe is designed to allow medical fluid from within the barrel thereof to be discharged from the syringe via the discharge tip.

7. The injector of claim 1, wherein the syringe is designed to allow medical fluid from within the barrel thereof to be discharged from the syringe via the discharge tip.

8. The injector of claim 5, wherein the low flow rate is no more than about 0.5 ml/sec.

9. The injector of claim 1, wherein the predetermined stop point is based on at least one parameter of the syringe.

10. The injector of claim 9, wherein the low flow rate is no more than about 0.5 ml/sec.

11. The injector of claim 1, wherein the predetermined stop point is user adjusted.

12. The injector of claim 11, wherein the low flow rate is no more than about 0.5 ml/sec.

13. The injector of claim 1, wherein the predetermined stop point is calibrated.

14. The injector of claim 13, wherein the low flow rate is no more than about 0.5 ml/sec.

15. The injector of claim 1, wherein the predetermined stop point is based on historical information.

16. The injector of claim 15, wherein the low flow rate is no more than about 0.5 ml/sec.

17. The injector of claim 1, wherein the low flow rate is applicable to a manual movement control of the injector.

18. The injector of claim 17, wherein the low flow rate is no more than about 0.5 ml/sec.

19. The injector of claim 1, wherein the low flow rate is applicable to an automatic purge of medical fluid from the syringe until the automatic purge is stopped by operator input.

20. The injector of claim 19, wherein the low flow rate is no more than about 0.5 ml/sec.

21. The injector of claim 1, wherein the processor is configured to advance the plunger drive ram to provide an initial flow rate until reaching the predetermined stop point, wherein the initial flow rate is a flow rate at which medical fluid is expelled from the discharge tip of the syringe due to the plunger drive ram moving the plunger within the barrel of the syringe, and wherein the initial flow rate is greater than the low flow rate.

22. A medical fluid injector comprising:
- a syringe comprising a barrel and a plunger, the barrel comprising a discharge tip, and the plunger being disposed within and movable relative to the barrel;
- a motorized plunger drive ram configured to move the plunger of the syringe within and relative to the barrel of the syringe both toward and away from the discharge tip of the syringe;
- a processor which controls movement of the plunger drive ram, the processor being configured with a purge sequence designed to force air and/or gas from the syringe via the discharge tip prior to fluidly connecting the syringe with a patient, the processor being further configured with an injection protocol designed to inject medical fluid into a patient when the syringe is fluidly connected with a patient; and
- a tilt sensor, wherein an output from the tilt sensor allows for execution of the purge sequence only when the discharge tip of the syringe is pointed upward, wherein an output from the tilt sensor allows for execution of the injection protocol when the discharge tip of the syringe is pointed downward, and wherein the purge sequence comprises:
  - a first purge portion comprising a programmed advancement of the plunger drive ram at a first purge flow rate and in a direction that moves the plunger within the barrel of the syringe and toward the discharge tip of the syringe; and
  - a second purge portion comprising advancement of the plunger drive ram at a second purge flow rate and in a direction that moves the plunger within the barrel of the syringe and toward the discharge tip of the syringe, the second purge portion being available only after completion of the first purge sequence segment, and the second purge flow rate being less than the first purge flow rate.

23. The injector of claim 22, wherein the second purge flow rate is no more than about 1 ml/sec.

24. The injector of claim 22, wherein the first purge portion further comprises terminating advancement of the plunger drive ram, and wherein user input is required to initiate the second purge portion.

25. The injector of claim 24, wherein the first purge portion is terminated upon reaching a predetermined stop point.

26. The injector of claim 22, wherein the second purge portion comprises using a hand-operated movement control associated with the plunger drive ram.

27. The injector of claim 22, wherein the second purge portion comprises a programmed advancement of the plunger drive ram.

* * * * *

UNITED STATES PATENT AND TRADEMARK OFFICE
CERTIFICATE OF CORRECTION

PATENT NO. : 7,771,389 B2  Page 1 of 1
APPLICATION NO. : 11/073892
DATED : August 10, 2010
INVENTOR(S) : Grispo et al.

It is certified that error appears in the above-identified patent and that said Letters Patent is hereby corrected as shown below:

Title Page, Item (56), Other Publications, delete "PCT/US2005/O04600" and insert therefor --PCT/US2005/004600--.
Column 7, line 15, delete "used" and insert therefor --use--.
Column 13, line 34, delete "5" and insert therefor --7--.

Signed and Sealed this

Fifth Day of October, 2010

David J. Kappos
*Director of the United States Patent and Trademark Office*